(12) United States Patent
Shou et al.

(10) Patent No.: US 8,999,928 B2
(45) Date of Patent: Apr. 7, 2015

(54) METHODS FOR TREATING DISEASES USING A BONE MORPHOGENETIC PROTEIN

(75) Inventors: Weinian Shou, Carmel, IN (US); Hanying Chen, Zionsville, IN (US); Loren J. Field, Indianpolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 13/262,180

(22) PCT Filed: Mar. 30, 2010

(86) PCT No.: PCT/US2010/029196
§ 371 (c)(1),
(2), (4) Date: Dec. 21, 2011

(87) PCT Pub. No.: WO2010/114833
PCT Pub. Date: Oct. 7, 2010

(65) Prior Publication Data
US 2012/0093776 A1    Apr. 19, 2012

Related U.S. Application Data

(60) Provisional application No. 61/165,721, filed on Apr. 1, 2009.

(51) Int. Cl.
*A61K 38/18* (2006.01)
*C07K 14/51* (2006.01)
*A61P 9/00* (2006.01)

(52) U.S. Cl.
CPC .................... *A61K 38/1875* (2013.01)

(58) Field of Classification Search
CPC ...... C07K 14/51; A61K 38/1875; A61F 2/82; A61F 2002/2817; A61F 2002/30601; A61F 2210/009
See application file for complete search history.

(56) References Cited

U.S. PATENT DOCUMENTS

| 6,818,210 | B2 * | 11/2004 | Field ............................ 424/93.21 |
| 2003/0224501 | A1 | 12/2003 | Young et al. |
| 2009/0017019 | A1 * | 1/2009 | Shields et al. .............. 424/133.1 |

OTHER PUBLICATIONS

Eckhouse et al., Biochem. Pharmacol., 2013, vol. 85(1):1-11.*
Oregon Health & Science University Newsletter, Apr. 29, 2004.*
Oh et al., PNAS, 2003, vol. 100(21):12313-12318.*
International Preliminary Report on Patentability mailed Oct. 13, 2011 from the International Bureau.
International Search Report completed by the U.S. Searching Authority on May 5, 2010 in connection with PCT/US2010/029196.
Aries et al. Essential role of GATA-4 in cell survival and drug-induced cardiotoxicity. PNAS< 2004, vol. 101, No. 18, pp. 6975-6980; Abstract; p. 6975, left col, last paragraph: p. 6977, left col, para 2-3; p. 6977-6978, "Parmacologic Modulation of GATA-4" Section.
Chen et al. Overexpression of Bone Morphogenetic Protein 10 in Myocardium Disrupts Cardiac Postnatal Hypertropic Growth. Journal of Biological Chemistry, 2006, vol. 281, No. 37, pp. 27481-27491; Abstract; p. 27481, Right column, para 2; p. 27490, right col, para1.

* cited by examiner

*Primary Examiner* — Xiaozhen Xie
(74) *Attorney, Agent, or Firm* — Barnes & Thornburg LLP

(57) ABSTRACT

Described herein are methods, uses, and pharmaceutical compositions for treating heart disease that include a bone morphogenetic protein (BMP). In addition, described herein are methods, uses, and compositions for preventing or slowing fibrosis in diseased or injured tissue, and/or for preventing or slowing cell death in diseased or injured tissue.

17 Claims, 6 Drawing Sheets

METHODS FOR TREATING DISEASES USING A BONE MORPHOGENETIC PROTEIN

CROSS REFERENCE TO RELATED APPLICATIONS

This application is a U.S. national counterpart application of international application serial No. PCT/US2010/029196 filed Mar. 30, 2010, which claims priority to U.S. Provisional Patent Application No. 61/165,721 filed Apr. 1, 2009. The entire disclosures of PCT/US2010/029196 and U.S. Ser. No. 61/165,721 are hereby incorporated by reference.

GOVERNMENT RIGHTS

This invention was made with government support under HL081092 and HL085098 awarded by the National Institutes of Health. The U.S. Government has certain rights in the invention.

TECHNICAL FIELD

The invention described herein relates to methods and compositions for treating heart disease that include a bone morphogenetic protein (BMP). In addition, the invention described herein relates to methods and compositions for preventing or slowing fibrosis in diseased or injured tissue. In addition, the invention described herein relates to methods and compositions for preventing or slowing cell death in diseased or injured tissue.

BACKGROUND AND SUMMARY OF THE INVENTION

Cardiovascular diseases are the leading cause of death worldwide. Heart failure can develop from a variety of pathological conditions, such as diseases, including but not limited to, hypertension, atherosclerosis, viral infections, cardiotoxic pharmacological agents, hypertrophy, and others, and/or injuries, such as including but not limited to, trauma, surgery, and others. Although such heart diseases and injuries may be caused by different etiological factors, once initiated, the general pattern of pathological progression of the diseases and/or injuries have similarities, such as the following illustrative sequence of events: (1) detrimental conditions or factors (2) cardiomyocyte insults or injuries (3) cardiomyocyte apoptosis and/or necrosis (4) cardiomyocyte death/dropout (5) recruitment of fibroblasts (6) increase of extracellular matrix deposition (7) cardiac fibrosis (8) possible impairment of cardiac contractile function (9) potential heart failure.

Fibrosis is characterized by a loss of normal tissue architecture and replacement with scar tissue. Either or both of those conditions may lead to organ failure. Fibrosis involves a multitude of cellular responses, one of which is the extracellular matrix deposition of collagen. Without being bound by theory, it is believed herein that fibroblasts play a primary role in the extracellular matrix deposition of collagen. It is further believed herein that cell apoptosis and/or cell necrosis leads to the recruitment of fibroblasts to the dead or dying cell, ultimately resulting in fibrosis. Without being bound by theory, it is believed herein that directly or indirectly decreasing, slowing, or preventing cardiac cells such as cardiomyocytes from undergoing apoptosis and/or necrosis may either slow or preclude the progression of diseased heart to heart failure, leading to a therapeutic benefit. In addition, though without being bound by theory, it is believed herein that directly or indirectly decreasing, slowing, or preventing excessive extracellular matrix deposition, such as from cardiac fibroblasts may also either slow or preclude the progression of diseased heart to heart failure, leading to a therapeutic benefit.

Currently, there are no known effective ways to reduce or reverse cardiac fibrosis. For example, though the use of β-blockers and angiotension-converting enzyme (ACE) inhibitors are used in the clinic, and can improve cardiac function, such a treatment has been reported to have a limited effect in preventing apoptosis or necrosis. Further, the efficacy of those drugs to reduce cardiac fibrosis has also been reported to be limited.

It has been discovered herein that bone morphogenetic proteins, such as BMPs-10, are potent cytokines having the capability of inhibiting cell apoptosis and/or necrosis, such as cardiomyocyte apoptosis and/or necrosis. It has also been discovered herein that BMPs-10 are potent cytokines having the capability of inhibiting extracellular matrix deposition by cardiac fibroblasts. It is appreciated herein that the dual activity of the bone morphogenetic proteins discovered herein may be useful in treating heart disease by a potential plurality of mechanisms, including directly inhibiting cardiac cell death, indirectly inhibiting fibrosis by inhibiting cardiac cell death, and/or directly inhibiting fibrosis.

In one illustrative embodiment of the invention, uses of a composition in the manufacture of a medicament for treating a heart disease or a heart injury, or a combination thereof, is described. In one illustrative aspect, the composition includes a therapeutically effective amount of a BMP-10, or alternatively one or more BMPs-10. In another embodiment, the composition also includes one or more carriers, diluents, and/or excipients.

In another illustrative embodiment, compositions are described herein for treating a heart disease or a heart injury, or a combination thereof. In one aspect, the compositions include a therapeutically effective amount of a BMP-10, or alternatively one or more BMPs-10.

In another illustrative embodiment, methods are described herein for treating a heart disease or a heart injury, or a combination thereof. In one aspect, the methods include the step of administering a composition comprising a therapeutically effective amount of a BMP-10, or alternatively one or more BMPs-10.

In another illustrative embodiment, pharmaceutical compositions are described herein. In one aspect, the compositions include a therapeutically effective amount of a BMP-10, or alternatively one or more BMPs-10, for treating a heart disease or a heart injury, or a combination thereof.

Figure 1A:
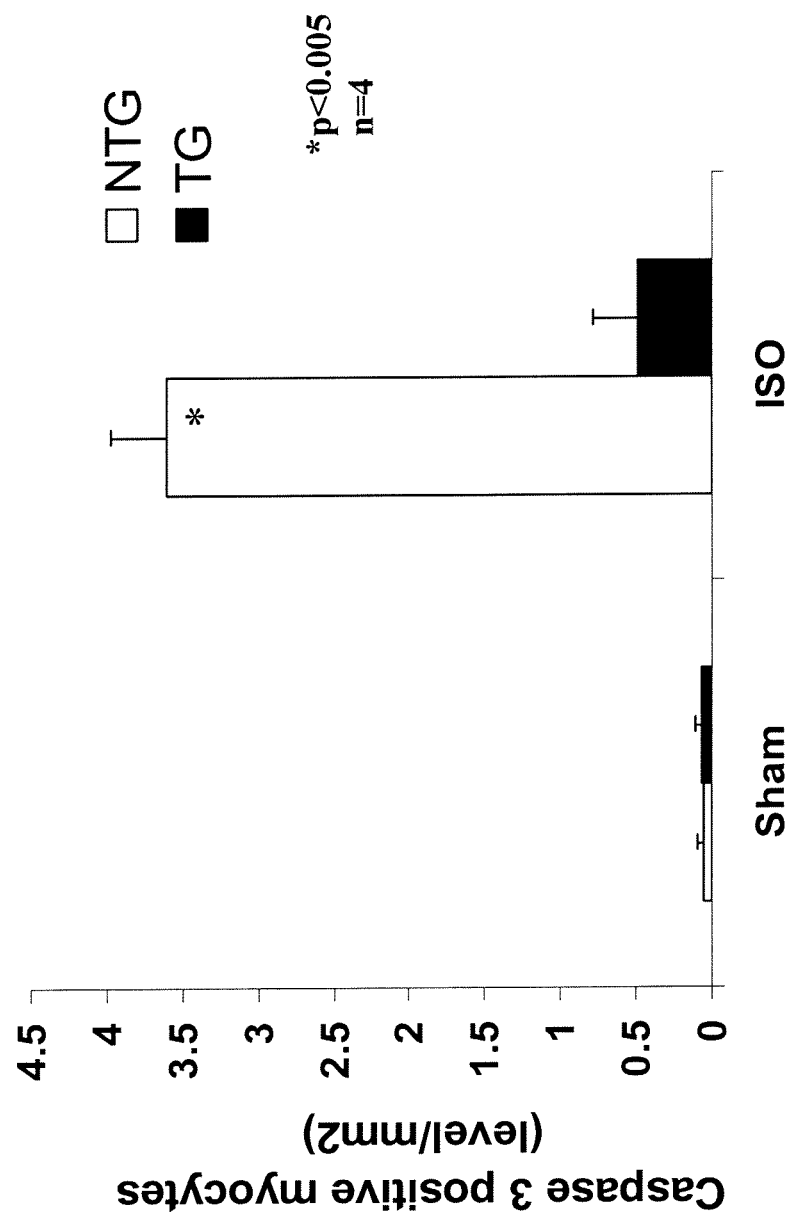
FIG. 1 (A) shows caspase-3 immunostaining in myocytes in BMP-10 transgenic (TG) and non-transgenic (NTG) mice in response to isoproterenol; (B) shows TUNEL positive myocytes in BMP-10 transgenic (TG) and non-transgenic (NTG) mice in response to isoproterenol.
Figure 1B:
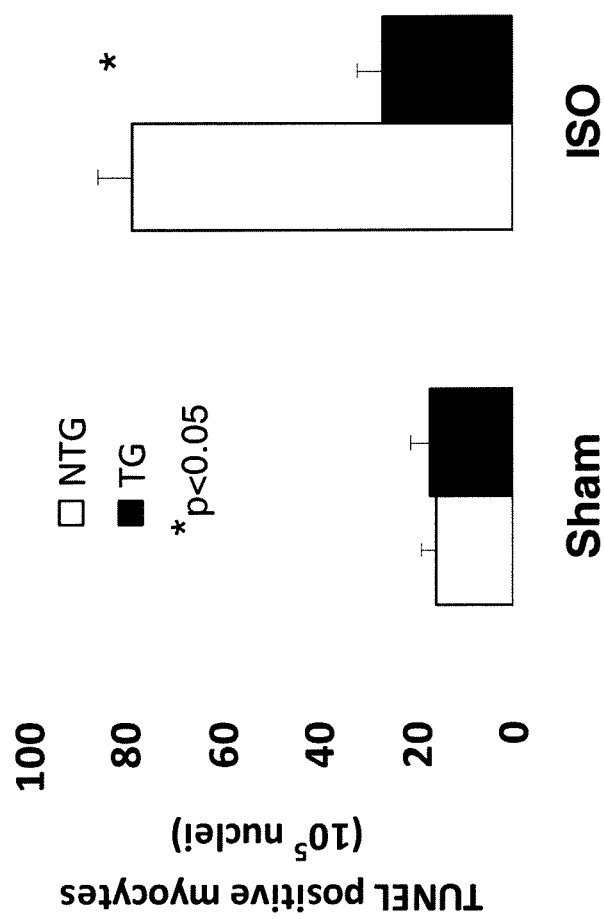

(B) shows the inhibition of isoproterenol induced increases in collagen type III mRNA levels in BMP-10 transgenic (TG) mice compared to non-transgenic (NTG) mice.

DETAILED DESCRIPTION

In one illustrative embodiment, a composition comprising a BMP-10, or a mixture thereof, is used in the manufacture of a medicament for treating a heart disease or a heart injury, or a combination thereof.

In another illustrative embodiment, a composition comprising a BMP-10, or a mixture thereof, for treating a heart disease or heart injury is described.

In another illustrative embodiment, a method for treating a heart disease or a heart injury, or a combination thereof is described. The method comprises the step of administering a composition comprising a therapeutically effective amount of a BMP-10, or a mixture thereof.

In another illustrative embodiment, a pharmaceutical composition is described. The pharmaceutical composition comprises a therapeutically effective amount of a BMP-10, or a mixture thereof, for treating a heart disease or a heart injury, or a combination thereof.

In one illustrative aspect, the BMP-10, or mixture thereof, is used to treat cardiac disease. Cardiac diseases that may be treated include, but are not limited to, cardiac disease resulting from hypertension, stenotic cardiac valve disorder, atherosclerosis, viral infection, or a genetic defect (e.g., a mutation that results in abnormal contractile proteins).

In another illustrative aspect, the BMP-10, or mixture thereof, is used to treat cardiac injury. Cardiac injury may result from one or more events including trauma, surgery or other medical procedure, the administration of a pharmacological agent, tissue damage arising from a disease or disease state, such as described herein, including but not limited to acute myocardial infarction, ischemia, or other events.

In another illustrative embodiment, a BMP-10 or a mixture thereof is administered to a patient in need thereof. The BMP-10 may be administered via stable tissue graft, injection, implanted device, or by gene delivery. The BMP-10 may be included in a matrix. It is to be understood that the BMP-10 or mixture thereof may be administered after the manifestation of a disease, or alternatively in advance of the manifestation of a disease or stage of a disease to a patient at risk of developing the disease or at risk of advancing to a more severe form of the disease. It is also to be understood that the BMP-10 or mixture thereof may be administered after the an injury has occurred, or in advance of an injury that is expected to occur or even planned, such as might occur during surgery or other medical procedure, or that might occur following the onset of a disease or disease state. Accordingly, it is to be understood that the methods, uses, and pharmaceutical compositions may be administered or performed prophylactically.

Illustratively, the BMP-10 or mixture thereof may be administered using stable tissue grafts of skeletal myoblasts and cardiomyocytes such as are described in U.S. Pat. No. 5,602,301, incorporated herein by reference in its entirety. In one illustrative aspect, the tissue graft includes undifferentiated cells, stem cells, progenitor cells, cardiomyocytes, myoblasts, cardiomyocyte progenitor cells, myoblast progenitor cells, or any combination thereof. The tissue graft may, for example, include autologous, isologous and/or allogeneic tissue. Illustratively, recombinant DNA technology is used to engineer these or other cells to express a BMP-10 for release into the host tissue following implantation.

Illustratively, the BMP-10 or mixture thereof may be administered parenterally. It is to be understood that all conventional methods of parenteral delivery as applicable to administering the compounds and compositions described herein. Illustrative parenteral methods include injection, the implantation of a device, including temporary, semi-permanent, and permanent, and other methods. Conventional methods for the parenteral delivery of peptides may be used for the compositions described herein, and in the methods described herein. In addition, methods of injecting solubilized or suspended peptides in formulation may be accomplished using all known techniques, including but not limited to parenteral, intravenous, and intracardial injections.

In another illustrative aspect, the BMP-10 or mixture thereof is administered via an implanted device. Such devices may be implanted permanently or temporarily depending on the desired duration of the BMP-10 treatment. Devices may be configured for sustained or intermittent release of the BMP-10, following a wide variety of dosing protocols both in terms of dose amount and the timing thereof.

In another illustrative aspect, one or more genes are delivered via a viral vector, such as rAAV (recombinant adeno-associate virus) gene delivery system (Chien (2006) *Novartis Found Symp.* 274:244-256). Such a system may provide sufficient treatment for the progression of heart failure.

The BMP-10 proteins are a subclass of the bone morphogenetic protein family, which is itself a subclass of polypeptides belonging to the TGF-β superfamily of proteins. As many as 20 BMPs have been reported. However, the BMPs-10 are distinguished from the other BMPs both structurally and functionally. One illustrative feature of BMP-10s, which may be used to distinguish for example BMP-2, BMP-4, BMP-5, BMP-6, BMP-7, and BMP-9, is that the gene encoding for human BMP-10 is located on chromosome 2 at p13.3.

BMPs-10 are also distinguished functionally from other proteins, including other BMPs by one or more activities in blocking cell death, such as apoptosis and/or necrosis, and/or in blocking the function of fibroblasts, and/or in blocking the signaling to other cells or recruitment of other cells by cells undergoing cell death, such as by apoptosis and/or necrosis. In another embodiment, BMPs-10 are described herein that are capable of blocking cell death, such as apoptosis and/or necrosis, and/or capable of blocking the function of fibroblasts, and/or capable of blocking the signaling to or recruitment of other cells by cells undergoing cell death, such as by apoptosis and/or necrosis. In another embodiment, BMPs-10 are described herein that are capable a dual effect of inhibition of apoptosis and inhibition of fibrosis. In each of the foregoing, in another variation, the BMPs-10 elicit the activity in vivo. It is appreciated that BMP-10 mediated inhibition of apoptosis can be determined, for example, in cardiomyocytes by detecting TUNEL, caspase-3, or other apoptosis markers in an assay in which a BMP-10 is coadministered with an apoptotic stimulatory treatment, such as the compounds isoproterenol, lipopolysaccharide, and the like or apoptotic inducing stimuli known in the art. BMP-10 mediated inhibition of fibrosis can be determined, for example, by measuring fibroblast proline incorporation, collagen expression or deposition, myocardial periostin immunostaining, or other markers of fibrosis in an assay in which BMP-10 is coadministered with a fibrosis stimulatory treatment, such as isoproterenol, or other fibrosis inducing stimuli known in the art.

Specific sequences of BMPs-10 have been described, such as in Neuhas et al. (1999) *Mech. Dev.* 80:181-184, the disclosure of which is incorporated herein by reference. In another embodiment, BMPs-10 are described herein that share a structural feature in a RRIR cleavage site. In another embodiment, BMPs-10 are described herein that comprise two polypeptide regions separated, or divided by an RRIR cleavage site. One polypeptide region may be a pro-region, and the other polypeptide region may be a mature region. In another illustrative embodiment, BMPs-10 are described herein that include a cysteine rich mature region. Illustratively, the cysteine rich region includes about 5, about 6, about 7, or about 8 cyteine residues. In another illustrative embodiment, BMPs-10 are described herein that include a cysteine rich mature region that includes about 7 cysteines.

In another illustrative embodiment, BMP-10 like peptides are described herein, including BMP-10 variants with minor structural changes including amino acid substitutions, deletions, truncations, and/or insertions that retain dual activity for inhibition of apoptosis and inhibition of fibrosis are used to inhibit apoptosis and/or fibrosis. However, it is to be understood that as used herein, the term BMP-10 includes such BMP-10 like peptides, unless otherwise specified, providing that such BMP-10 like peptides are capable of exhibiting one of more of the functional properties described herein, such as the capability of blocking cell death, such as apoptosis and/or necrosis, and/or in blocking the function of fibroblasts, and/or in blocking the signaling to other cells or recruitment of other cells by cells undergoing cell death, such as by apoptosis and/or necrosis.

In another illustrative embodiment, methods, uses, and compositions that include a BMP-10, or a combination thereof, are described for use in inhibiting apoptosis of cardiomyocytes.

In another illustrative embodiment, methods, uses, and compositions that include a BMP-10, or a combination thereof, are described for use in inhibiting fibrosis.

In another illustrative embodiment, methods, uses, and compositions that include a BMP-10, or a combination thereof, are described for use in inhibiting both apoptosis and fibrosis.

In another illustrative embodiment, methods, uses, and compositions that include a BMP-10, or a combination thereof, are described for use in inhibiting the deposition of collagen by fibroblasts.

In another embodiment, methods, uses, and compositions that include a BMP-10, or a combination thereof, are described for use in inhibiting more than about 50% of cardiomyocyte apoptosis.

In another embodiment, methods, uses, and compositions that include a BMP-10, or a combination thereof, are described for use in inhibiting about 75% or more cardiomyocyte apoptosis.

In another embodiment, methods, uses, and compositions that include a BMP-10, or a combination thereof, are described for use in inhibiting about 90% or more cardiomyocyte apoptosis.

In another embodiment, methods, uses, and compositions that include a BMP-10, or a combination thereof, are described for use in inhibiting substantially all cardiomyocyte apoptosis.

In another embodiment, methods, uses, and compositions that include a BMP-10, or a combination thereof, are described for use in completely inhibiting cardiomyocyte apoptosis.

In another embodiment, methods, uses, and compositions that include a BMP-10, or a combination thereof, are described for use in inhibiting more than about 50% of fibrosis.

In another embodiment, methods, uses, and compositions that include a BMP-10, or a combination thereof, are described for use in inhibiting about 75% or more of fibrosis.

In another embodiment, methods, uses, and compositions that include a BMP-10, or a combination thereof, are described for use in inhibiting about 90% or more of fibrosis In another embodiment, methods, uses, and compositions that include a BMP-10, or a combination thereof, are described for use in substantially inhibiting fibrosis.

In another embodiment, methods, uses, and compositions that include a BMP-10, or a combination thereof, are described for use in completely inhibiting fibrosis.

It is appreciated herein that the degree of inhibition of apoptosis or fibrosis can be evaluated based evaluation of effects on cellular markers for apoptosis and fibrosis according to conventional techniques. Illustratively, assays for apoptosis include but are not limited to TUNEL and caspase 3 staining. Illustratively, assays for fibrosis and collagen deposition include but are not limited to Mason-Trichome staining, periostin staining, and proline uptake assays. It is appreciated that the foregoing may be evaluated by visual observation, quantification, image analysis (e.g. optical density), scoring scale, or other techniques known in the art. For example, a scoring scale can be used to evaluate efficacy for inhibition of apoptosis or fibrosis wherein levels of staining density or intensity are ranked from lower to higher, for example, from 1-5, wherein, illustratively, 1 represents faint/no staining, 2 represents light staining, 3 represents medium staining, 4 represents moderately high staining, and 5 represents very high staining, inversely indicative of efficacy of inhibition.

As used herein, the term therapeutically effective amount generally refers to an amount of a BMP-10 that is capable of inhibiting apoptosis and/or extracellular matrix deposition of proteins, each at varying levels that may be determined by an attending physician and/or diagnostician to provide an overall benefit in the health of or to the patient.

As used herein, the term "inhibiting" generally refers to preventing, blocking, stopping, and/or slowing the progression in any manner, including partially or completely reversing.

Without being bound by theory, it is believed herein that the effects of cardiac trauma or disease may lead to, or be exacerbated by, an apoptotic or necrotic loss of cardiomyocytes. In addition, loss of cardiomyocytes may be accompanied by recruitment of fibroblasts, and the upregulation of fibroblasts can lead to the deleterious release of extracellular matrix proteins commonly released by fibroblasts, including, for example, collagens Type I and III, which may cause tissue scarring. It has been discovered herein that the administration of a BMP-10, or a combination thereof may inhibit apoptosis of cardiac myocytes as well as inhibit extracellular matrix deposition of proteins by fibroblasts, thereby slowing the progression, stopping, or preventing heart failure.

Without being bound by theory, it is also believed herein that the therapeutic efficacy of BMP-10 in preventing fibrotic tissue formation may lie in one or both of two biological processes. BMP-10 has been observed herein to block and/or antagonize cell apoptosis. Such blocking and/or antagonism may decrease the response of fibroblasts due to lower injury. It is appreciated that such a decreased fibroblast response may lead to a decrease or complete block of fibrotic tissue formation. BMP-10 has also been observed herein to block and/or antagonize the ability of fibroblasts to secrete and/or synthesize collagen. It is appreciated that fibrotic tissue formation may be dependent upon the ability of fibroblasts to secrete and/or synthesize collagen. It is also appreciated that blocking or inhibiting to some extent both pathways may be advantageous. Complete blockage of apoptosis in patients already suffering from hypertrophy may be deleterious due to the concomitant removal of the patient's ability to clear excess tissue. Accordingly, inhibition of apoptosis coupled with inhibition of collagen synthesis or secretion may be an alternate embodiment for some patients.

Data has been obtained indicating biological activities of BMP-10 in vivo using transgenic animals to deliver BMP-10 to the myocardium (cardiac myocytes, involuntary striated muscle found in the heart wall). Overexpression of BMP-10 in myocardium disrupts cardiac postnatal hypertrophic growth in transgenic mice. However, BMP-10 was not found to inhibit eutrophic increases in cardiac mass resulting from chronic exercise, nor does it appear to alter the increase in cardiac size caused by isoproterenol treatment upon gross morphological examination (Chen et al. (2006) *Journal of Biological Chemistry* 281:27481-27491, herein incorporated by reference).

The experiments described herein collectively demonstrate that BMP-10 can antagonize cardiomyocyte apoptosis in response to several adverse stimuli in vivo. Moreover, BMP-10 antagonizes cardiac fibrosis in vivo. Without being bound by theory, it is believed that the observation that BMP-10 can attenuate collagen synthesis in ACFs (adult cardiac fibroblasts) induced by TGFβ in vitro suggests that the cardioprotective activities of BMP-10 result from a combination of anti-apoptotic activity and inhibition of extracellular matrix formation. The ability of a single molecule to impart dual cardioprotective effects (anti-apoptosis and inhibition of collagen synthesis) is believed herein to be a unique quality of BMP-10. Thus, BMP-10 serves as a useful therapeutic reagent for treating fibrosis in the heart. Additionally, BMP-10 may be used as a co-therapy for treating diseases that are known to ultimately result in fibrotic tissue formation in the heart.

EXAMPLES

Example 1

BMP-10 inhibits cardiomyocyte apoptosis in response to cardiac injuries. To study the impact of BMP-10 expression in the postnatal ventricular myocardium, cardiac restricted BMP-10 transgenic mice were generated using the alpha-myosin heavy chain (MHC) promoter. Five transgenic lines carrying the MHC-BMP-10 transgene were generated, each with similar levels of BMP-10 expression. Initial characterization of the transgenic mice indicates BMP-10 is able to block developmental hypertrophy, which results in a smaller heart in MHC-BMP-10 transgenic mice. The initial description of these mice is found in Chen et al. (2006) *Journal of Biological Chemistry* 281:27481-27491. Overexpression of BMP-10 in myocardium was found to disrupt cardiac postnatal hypertrophic growth. To investigate if BMP-10 expression would alter the ability of cardiomyocytes to respond to hypertrophic stimuli, three month old transgenic mice were treated with the beta-adrenergic agonist isoproterenol using a 7 day infusion osmotic minipump (0.028 g/mL isoproterenol in saline at flow rate of 1 mL/hr). This treatment typically results in 1) an approximately 30-40% increase in heart weight/body weight ratio which is reflected by uniform hypertrophic cardiomyocyte growth; 2) profound cardiac fibrosis, a result of cardiomyocyte apoptosis and extracellular matrix deposition. A marked and proportionally similar increase in cardiac mass was found to be apparent in both non-transgenic and MHC-BMP10 animals treated with isoproterenol, suggesting that BMP-10 does not affect pathological hypertrophy.

Cardiac fibrosis is found herein to be dramatically reduced in isoproterenol treated MHC-BMP-10 hearts when compared to treated non-transgenic hearts as demonstrated by Mason-Trichrome staining. Regions of greater collagen deposition in NTG and greater anti-periostin immunostaining (a cardiac fibroblast marker) are observed, whereas MHC-BMP-10 hearts have almost no positive staining signals for both collagen deposition and periostin production.

Also tested was whether BMP-10 is able to inhibit cardiomyocyte apoptosis in isoproterenol treated heart. Activated caspase 3 immune staining and TUNEL staining indicated that cardiomyocyte apoptosis was significantly less in the isoproterenol treated MHC-BMP-10 mice as compared to their non-transgenic littermates (FIG. 1A,B). Transgene expression reduced isoproterenol-induced caspase activity 0.49±0.39 cells per mm$^2$ in transgenic mice vs. 3.6±0.37 cells per mm$^2$ in non-transgenic mice, n=4 mice each, p<0.05). Similar results were obtained with TUNEL staining. Positive TUNEL staining was observed in NTG, with fewer or no TUNEL stained cells found in matched regions in MHC-BMP-10. Thus, without being bound by theory, it appears that BMP-10 activates a survival pathway in postnatal hearts. In support of this conclusion, Western blot analysis of anti-apoptotic members of Bcl family proteins revealed that Bcl-XL levels were significantly elevated in MHC-BMP-10 hearts. In addition, the level of cleaved Parp (a specific caspase target) was significantly lower in transgenic heart treated with isoproterenol compared to non-transgenic heart, which further confirms the lower apoptotic activity in MHC-BMP-10 heart.

Figure 2:
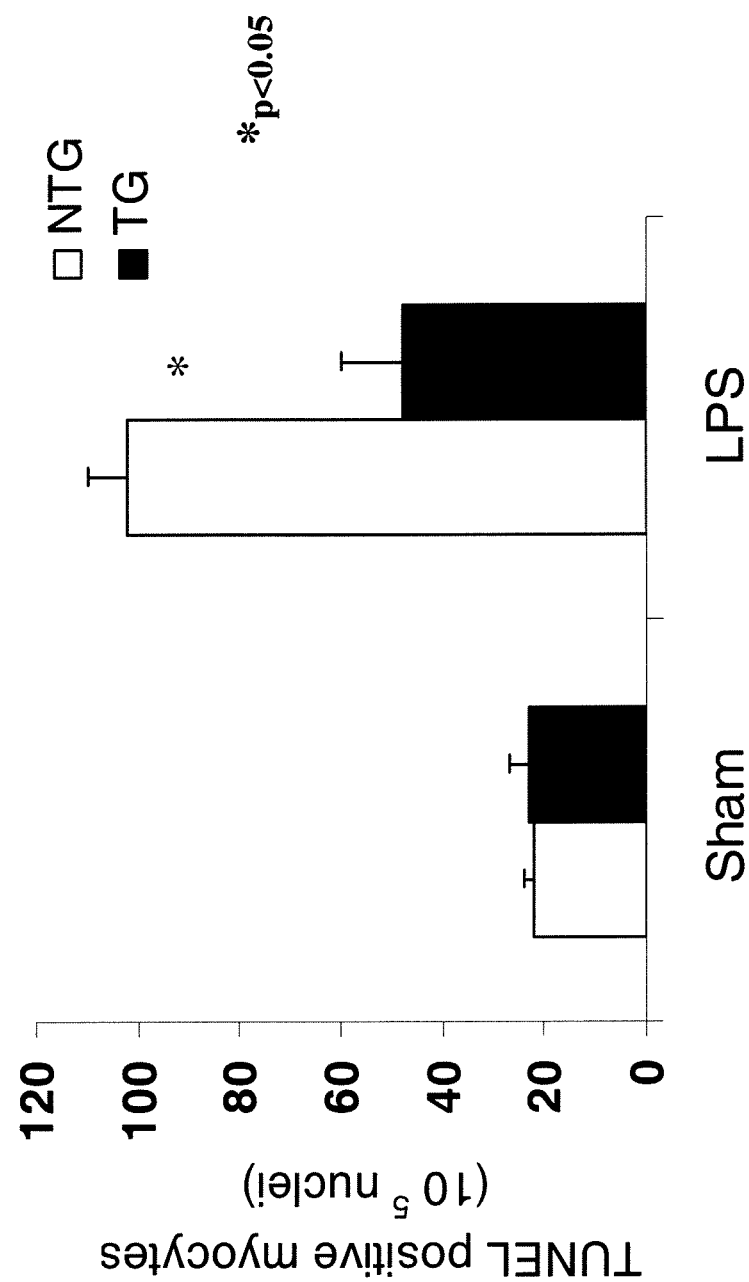
FIG. 2 shows TUNEL positive myocytes in BMP-10 transgenic (TG) and non-transgenic (NTG) mice in response to lipopolysaccharide (LPS).

To test whether this anti-apoptotic activity can be seen in a different cardiac injury model, the impact of BMP-10 expression on endotoxin-induced inflammatory-mediated cell death was investigated. A single dose of lipopolysaccharide (LPS), an endotoxin, (5 micrograms/gram IP in saline) induced prominent apoptosis in non-transgenic mice within 24 hours as evidenced by TUNEL staining (FIG. 2).

In contrast, LPS treated MHC-BMP-10 hearts had significantly less apoptosis. Moreover, Western blot analysis reveals that Bcl-XL was up-regulated in LPS-treated MHC-BMP-10 transgenic hearts, but not in LPS-treated non-transgenic hearts. A profound inflammatory response accompanies viral myocarditis and other cardiac injuries that induce cardiomyocyte apoptosis. BMP-10 may antagonize cardiomyocyte apoptosis resulting from various cardiac injuries.

Example 2

Figure 3:
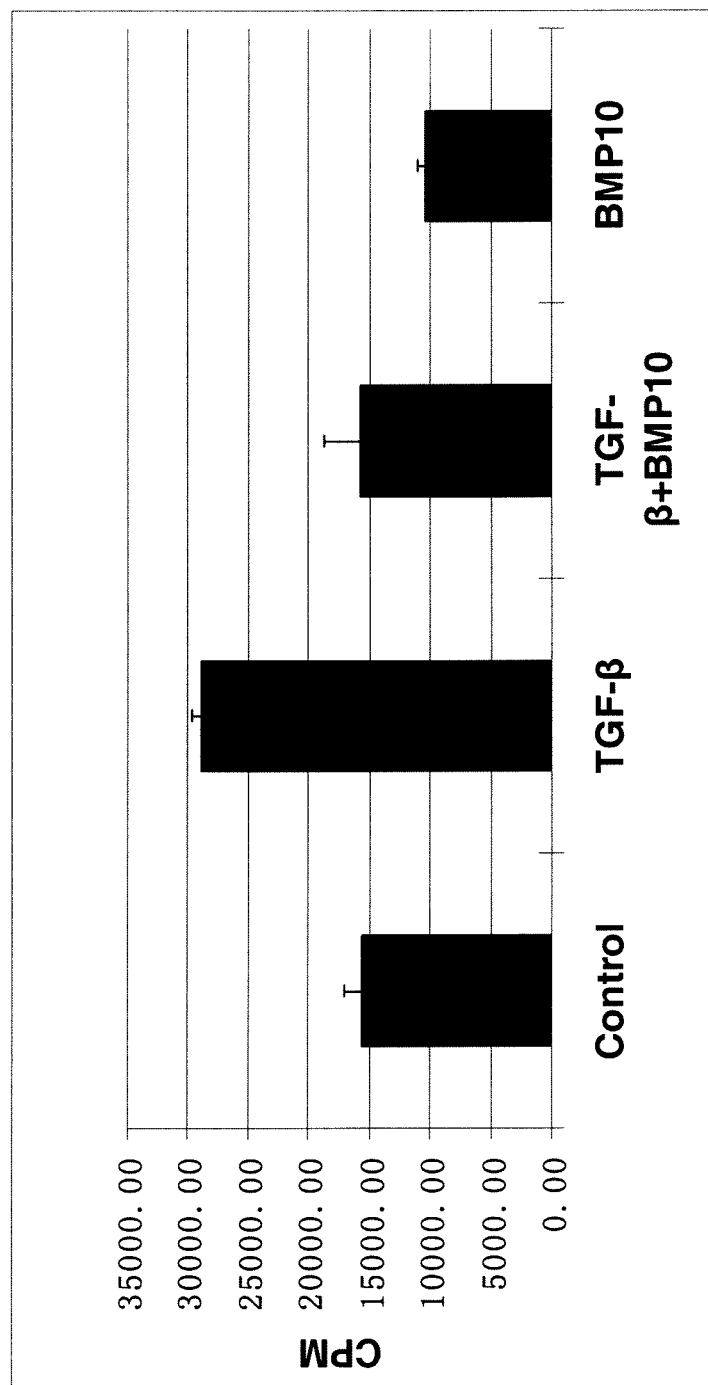
FIG. 3 shows the effect of BMP-10 on [$^3$H]-proline incorporation in adult cardiac myocytes.
Figure 4:
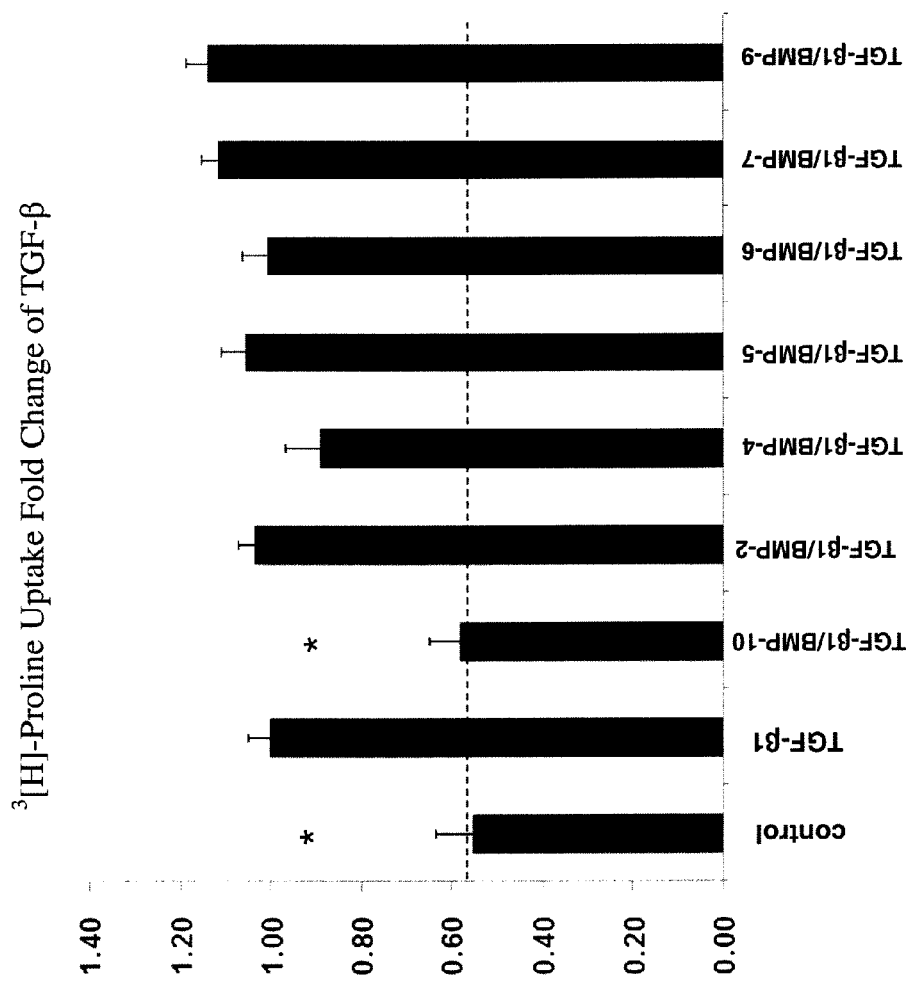
FIG. 4 shows the effect of BMPs on TGF-β1 induced [$^3$H]-proline uptake in adult cardiac myocytes.
Figure 5:
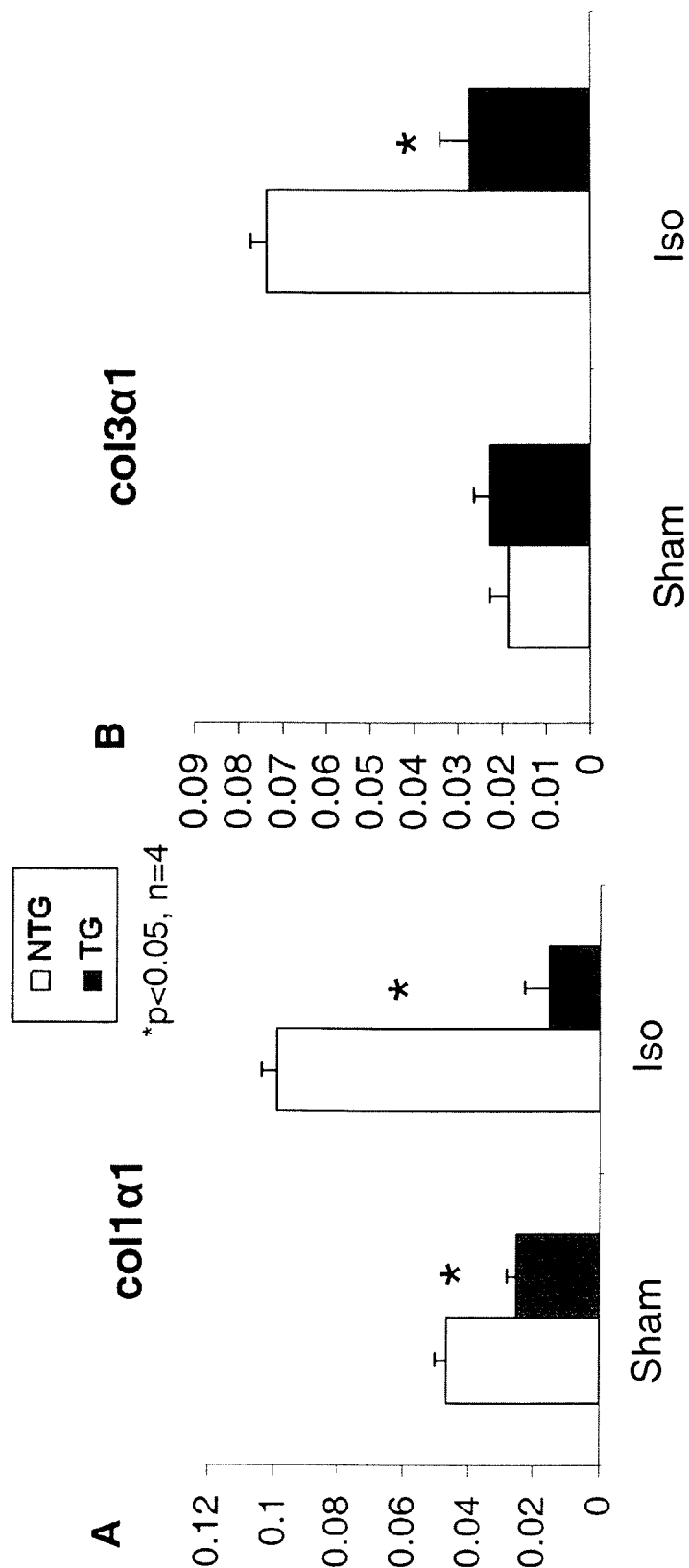
FIG. 5 (A) shows the inhibition of isoproterenol induced increases in collagen type I mRNA levels in BMP-10 transgenic (TG) mice compared to non-transgenic (NTG) mice.

BMP-10 inhibits extracellular matrix synthesis and deposition. It has been reported that a disproportionate increase in synthesis and/or inhibition of degradation of extracellular matrix (ECM) proteins in the interstitial space causes cardiac fibrosis. The major ECM proteins in the myocardium are type I and type III collagens, and represent approximately 90% of the collagen present in the heart. Cardiac myocytes comprise only 40% of the total number of cells in the heart; while cardiac fibroblasts comprise the majority of the remaining cells (vascular and neuronal cells are also present). Cardiac fibroblasts produce growth factors, cytokines, as well as ECM proteins and proteases, which collectively play a role in cardiac inflammation, tissue repair, and fibrosis. To determine whether BMP-10 has an effect on collagen synthesis in adult cardiac fibroblasts (ACFs), a [$^3$H]-Proline incorporation assay (a standard assay for collagen production) was performed. Transforming growth factor (TGF)-β1 is shown to be a potent enhancer for collagen production in ACFs (FIG. 3). This activity is inhibited by BMP-10. It is further confirmed that, in comparison to other BMP members (e.g., BMP-2, -4, -5, -6, -7, and -9), BMP-10 is the only BMP member has this inhibitory activity for collagen production (FIG. 4). At the transcriptional level, BMP10 inhibits two major collagens in the heart, collagen type I (col1α1) and III (col3α1) mRNA levels as assessed by quantitative RT-PCR (FIG. 5).

It has been reported that TGFβ plays an important role in cardiac fibrosis. In response to pressure overload TGFβ production increases in both the cardiomyocytes and cardiac myofibroblasts, which enhances β-adrenergic receptor (βAR) activity in cardiomyocytes and produces more extracellular matrix (ECM) in cardiac myofibroblasts. These dual processes will lead cardiac hypertrophy, cardiomyocyte apoptosis, and fibrosis. Our data indicate that BMP-10 is a potent factor in inhibiting both cardiomyocyte apoptosis and fibrosis.

Inbred mice of the DBA/2J strain give rise to spontaneous cardiac fibrosis due to their unique genetic lesions. However, BMP-10 transgenic mice of the DBA/2J strain do not develop cardiac fibrosis, which indicates that BMP-10 is a strong anti-fibrotic reagent in the heart.

Example 3

BMP-10 administration via tissue graft. Cellular transplantation technology is used to provide stable grafts in the heart as well as enable the delivery of useful recombinant proteins directly into the heart. Myoblasts, cardiomyocytes, or other cell types are maintained in the undifferentiated state by culturing at low density in high glucose Dulbecco's Modified Eagle media (DMEM) supplemented with 20% fetal bovine serum, 1% chicken embryo extract, 100 units/mL penicillin and 100 μg/mL streptomycin. Differentiation is induced by culturing in DMEM supplemented with 2% horse serum and antibiotics.

A fusion gene comprising an alpha-myosin heavy chain promoter, or other suitable promoter, driving BMP-10 cDNA is used to produce stably transfected BMP-10 expressing cells. The fusion gene is introduced into target cells by calcium phosphate transfection. Independent clones are isolated and the presence of the transgene is confirmed by Southern blot analysis. The relative expression of BMP-10 in each line is assessed by Northern blot to select a clone with suitable levels of BMP-10 expression.

BMP-10 expressing cells are isolated by enzymatic digestion and cultured in PC-1 medium containing 10% fetal calf serum. Cells are labeled with 10 μM 8-chloromethyl-4,4-difluoro-1,3,5,7-tetramethyl-4-bora-3a,4adiazaindecene for 30 minutes at 37° C. to facilitate localization of the injection site. Before injection, cells are harvested with trypsin and collagenase and washed in serum-free PC-1 medium. A graft comprising the BMP-10 expressing cells is directly injected into the myocardium under open heart surgery.

What is claimed is:

1. A method for treating a heart injury, wherein the heart injury comprises cardiac fibrosis, the method comprising the step of administering a composition comprising a therapeutically effective amount of a bone morphogenic protein-10 (BMP-10) protein, where the administering step is performed by injection or by tissue graft, or a combination thereof.

2. The method of claim 1 wherein the injury is caused at least in part by the administration of one or more pharmacological agents.

3. The method of claim 1 wherein the injury is the result of at least in part of trauma, acute myocardial infarction, or ischemia.

4. The method of claim 1 wherein the BMP-10 protein is administered parenterally.

5. The method of claim 4 wherein the BMP-10 protein is administered by intracardial injection.

6. The method of claim 4 wherein the BMP-10 protein is administered by intravenous injection.

7. The method of claim 1 wherein the BMP-10 protein is administered via an implanted device.

8. The method of claim 1 wherein the BMP-10 protein is administered by a tissue graft incorporating the BMP-10 protein.

9. The method of claim 8 wherein the tissue graft comprises undifferentiated cells.

10. The method of claim 8 wherein the tissue graft comprises stem cells.

11. The method of claim 8 wherein the tissue graft comprises progenitor cells.

12. The method of claim 8 wherein the tissue graft comprises cardiomyocyte progenitor cells.

13. The method of claim 8 wherein the tissue graft comprises myoblasts or cardiomyocytes.

14. The method of claim 8 wherein the tissue graft comprises an autograft.

15. The method of claim 1 wherein the BMP-10 protein is included in a matrix.

16. The method of claim 1 wherein the therapeutically effective amount is sufficient to reduce cardiomyocyte apoptosis.

17. The method of claim 1 wherein the therapeutically effective amount is sufficient to reduce cardiac fibrosis.

* * * * *